(12) United States Patent
Duke et al.

(10) Patent No.: US 8,449,460 B2
(45) Date of Patent: May 28, 2013

(54) TROCAR

(75) Inventors: Daniel H. Duke, Franklin, OH (US); Shailendra K. Parihar, Mason, OH (US); Randall J. Tanguay, Lebanon, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 38 days.

(21) Appl. No.: 13/053,845

(22) Filed: Mar. 22, 2011

(65) Prior Publication Data

US 2011/0237901 A1 Sep. 29, 2011

Related U.S. Application Data

(60) Provisional application No. 61/316,525, filed on Mar. 23, 2010.

(51) Int. Cl.
*A61B 1/32* (2006.01)

(52) U.S. Cl.
USPC .......................................................... 600/208

(58) Field of Classification Search
USPC .......................................................... 600/208
See application file for complete search history.

(56) References Cited

U.S. PATENT DOCUMENTS

| | | | | |
|---|---|---|---|---|
| 5,657,963 | A | * | 8/1997 | Hinchliffe et al. .......... 251/149.1 |
| 7,481,765 | B2 | * | 1/2009 | Ewers et al. .................. 600/208 |
| 8,012,129 | B2 | * | 9/2011 | Bettuchi et al. .......... 604/167.06 |
| 2005/0070947 | A1 | | 3/2005 | Franer et al. |
| 2009/0036745 | A1 | * | 2/2009 | Bonadio et al. ............... 600/208 |

* cited by examiner

*Primary Examiner* — Eduardo C Robert
*Assistant Examiner* — James Palmer (57) ABSTRACT

A surgical access device, such as a trocar, is described. The trocar includes a first housing member selectively coupled to a second housing member, such as with a latching assembly, and a seal which can be compressed when the housing members are coupled together, the seal for preventing or reducing transverse escape of insufflation gas or other fluid from between the coupled together first and second members.

8 Claims, 12 Drawing Sheets

TROCAR

RELATED APPLICATIONS

This application claims the benefit of U.S. provisional application No. 61/316,525 filed 23 Mar. 2010.

CROSS REFERENCE TO RELATED APPLICATION

This application cross references and incorporates by reference commonly assigned U.S. patent application Ser. No. 10/943,222 filed Sep. 17, 2004, and published as US2005/0070947.

FIELD OF THE INVENTION

The invention relates to access devices, such as trocars. More particularly, the invention relates to sealing between separable components of trocars, such as to prevent or reduce fluid leakage and assist in maintaining insufflation.

BACKGROUND

A trocar assembly is a surgical instrument that is used to gain access to a body cavity. A trocar assembly generally comprises two major components, a trocar sleeve, composed of a trocar housing and a trocar cannula, and a trocar obturator. The trocar cannula, having the obturator inserted therethrough, is directed through the skin to access a body cavity. Once the body cavity is accessed, laparoscopic or arthroscopic surgery and endoscopic procedures may be performed. In order to penetrate the skin, the distal end of the trocar cannula is placed against the skin that has been previously cut with a scalpel. The trocar obturator is then used to penetrate the skin and access the body cavity. By applying pressure against the proximal end of the trocar obturator, the sharp point of the trocar obturator is forced through the skin until it enters the body cavity. The trocar cannula is inserted through the perforation/incision made by the trocar obturator and the trocar obturator is withdrawn, leaving the trocar cannula as an access way to the body cavity.

The proximal end portion of the trocar cannula is typically joined to a trocar housing that defines a chamber having an open distal end portion in communication with the interior lumen defined by the trocar cannula. Elongated surgical instruments axially extend into and are withdrawn from the trocar cannula through the proximal end portion of the chamber defined by the trocar housing.

As those skilled in the art will certainly appreciate, many trocar housings are formed with first and second housing members. The first housing member may include an instrument seal for providing a seal about an instrument inserted through the trocar housing, and the second housing member may include a zero closure seal assembly, such as a duckbill seal assembly, for preventing escape of insufflations gas when no instrument is inserted through the trocar. It will be understood by those skilled in the art that such instrument seals and duckbill seals are employed to prevent escape of insufflations gas in an axial (longitudinal) direction from the body cavity, through the trocar cannula and housing, to the outside environment (along a direction generally parallel to the long axis of the cannula of the trocar.)

The first and second housing members may be selectively coupled together in a way that the first and second members may be separated, one from the other, to facilitate various surgical procedures. For example, it is often desirable to remove the first housing member during the removal of a specimen. The removal of the first housing member allows the specimen to pass through only the duckbill seal assembly, instead of passing through both the duckbill seal assembly and the proximal seal assembly. This provides for easier specimen removal and less trauma to the specimen during the removal process. The above incorporated patent application US 2005/0070947 discloses a trocar housing assembly having a first housing member selectively coupled to a second housing member.

During certain surgical procedures, such as bariatric procedures, relatively high bending and/or torsional loads may be placed on the trocar housing, such as when an instrument is inserted through the trocar, and the instrument and/or trocar is manipulated (e.g. by applying a force or torque to the instrument or trocar to rotate or pivot the trocar within the perforation/incision) to access/reach the required tissue in high body mass index (BMI) patients.

While having separable first and second seal housing members provides for convenient specimen removal, the interface between the first and second sealing members may provide a potential radial leak path of insufflations gas, especially when bending or torsional loads are applied to the trocar housing.

SUMMARY

Applicant has recognized the desirability of providing separable first and second housing members in combination with a deformable seal, such as gasket seal operable to reduce leakage of insufflations gas or other fluids from between the first and second housing members when the trocar housing is subjected to torsion and bending loads.

Applicant has also recognized the desirability of providing a deformable seal which is compressed when the separable housing members are releasably joined together, such as with a latching assembly, and where the seal is configured so as to not require an excessive compressive force or clamping force for joining the first and second housing members.

Still further the Applicant has also recognized the desirability of providing a seal where at least a portion of the seal is spaced radially from the outer perimeter of at least one of the instrument seal and the duckbill seal. Still further, the Applicant has also recognized the desirability of providing an inter-housing member seal, at least a portion of which is non-circular, and where the inter-housing member seal has a long axis (major axis) which is oriented with respect to a latch feature for joining the housing members, such as where the long axis of the seal extends substantially perpendicular to a latching axis of the first and second housing members, and such that the long axis of the seal is generally perpendicular to an axis about which one housing member may pivot with respect to the other housing member when the housing members are releasably joined together, such as by a latch assembly.

In one embodiment, the invention provides a surgical access device, such as a trocar, having first and second housing member, and a deformable, compressible seal disposed for sealing between opposed faces of the members when the members are joined together, such as with a latching assembly. The seal can be configured so that the seal is compressed when the first and second housing members are joined together, such that seal is provided with (or otherwise induced to have) a compressive load for counter-acting in-use torsional and bending forces applied to the trocar, which forces might otherwise result in a leak gap between the first and second housing members. Accordingly, the seal's compressive load may be employed to help prevent separation of, and fluid leakage from between, the first and second housing members.

In one non-limiting embodiment, the seal comprises a relatively compressible, relatively lower hardness gasket seal overmolded with one of the housing members, such that the gasket seal includes a portion extending from a groove or other recess formed in a relatively higher hardness surface of one of the housing members.

In one embodiment, the seal may have a perimeter, at least a portion of which is non-circular, and the seal may further comprise a circular portion surrounding and radially offset from a channel through which instruments pass. The seal may have a long axis (major) axis oriented with respect to a latching feature, such that the seal may resist bending/torsion about a latching axis of the first and second housing members.

In one non-limiting embodiment, the seal comprises a relatively low durometer (low hardness) gamma sterilizable silicone having a durometer of less than about 15 Shore A, and more particularly less than or equal to about 10 Shore A, and in one embodiment between about 4 and about 6 shore A. The seal may be configured such that a clamping force of no more than about 15 pounds, and more particularly no more than about 10 pounds is required to push together and latch (or otherwise join) the first and second housing members.

In one non-limiting embodiment, the gasket seal is overmolded in a groove or other recess formed in a face of one of the housing members, with the groove having a height between about 0.010 and about 0.025 inch, (more particularly between about 0.015 inch and about 0.020 inch inclusive), and a groove width of about 0.050 inch to about 0.075 inch. The gasket seal can have a rounded/hemispherical top, and in an uncompressed state, the gasket seal can extend above the surface in which the groove is formed a height of between about 0.020 inch and about 0.050 inch, and more particularly, between about 0.025 inch and about 0.045 inch.

DETAILED DESCRIPTION

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

FIGS. 1-5 illustrate a trocar assembly as disclosed in US Patent Publication US 2005/0070947, incorporated herein by reference in its entirety. FIGS. 1-5 and the associated description are provided for reference. FIG. 6-16 illustrate a trocar according to one non-limiting embodiment of the present invention.

Trocar of US Publication 2005/0070947

Referring to FIGS. 1 to 5, the trocar assembly 10 as shown in US 2005/0070947 generally includes a trocar cannula 12, a trocar obturator 14, and a trocar housing (or handle) 16. The trocar cannula 12 defines an interior lumen 18 having an open distal end portion 20 and an open proximal end portion 22. The proximal end portion 22 extends into and is mounted in the distal end portion 24 of trocar housing 16.

The trocar housing 16 has an open proximal end portion 26 that defines an opening 28. (See FIG. 2). The opening 28 communicates with a proximal seal assembly 30, which may include an instrument seal for sealing about an instrument shaft inserted in opening 28. A zero closure seal assembly, such as a duckbill seal assembly 32 is shown positioned beneath (distal of) the seal assembly 28.

In general, the trocar sleeve 44 is composed of a trocar cannula 12 and a trocar housing 16. The trocar housing 16 is shown including first housing member 36 and a second housing member 38. The first and second housing members 36/38 may be releasably secured to one another, such that the first housing member 36 may be separated from the second housing member 38, and then re-secured to one another if desired, as described more fully below.

The distal tip of the trocar obturator 14 can be inserted through the opening 28 of the housing 16, through the proximal seal assembly 30, through the duckbill seal assembly 32, and through an axial passageway in the trocar cannula 12, such that the distal tip of the obturator 14 extends through the open distal end of the cannula 12. An obturator handle 34 is provided at the proximal end of the trocar obturator 14 and a point or blade (not shown) may be included at the distal end of the obturator. As is well known in the art, the proximal seal assembly 30 cooperates with the exterior of the instruments (for example, trocar obturators and other tools adapted for use in conjunction with trocar based procedures) extending through the trocar to sealingly engage the exterior surface thereof and thereby preclude the passage of fluids (including liquids and insufflations gas) in an axial direction through the trocar housing 16.

Figure 1:
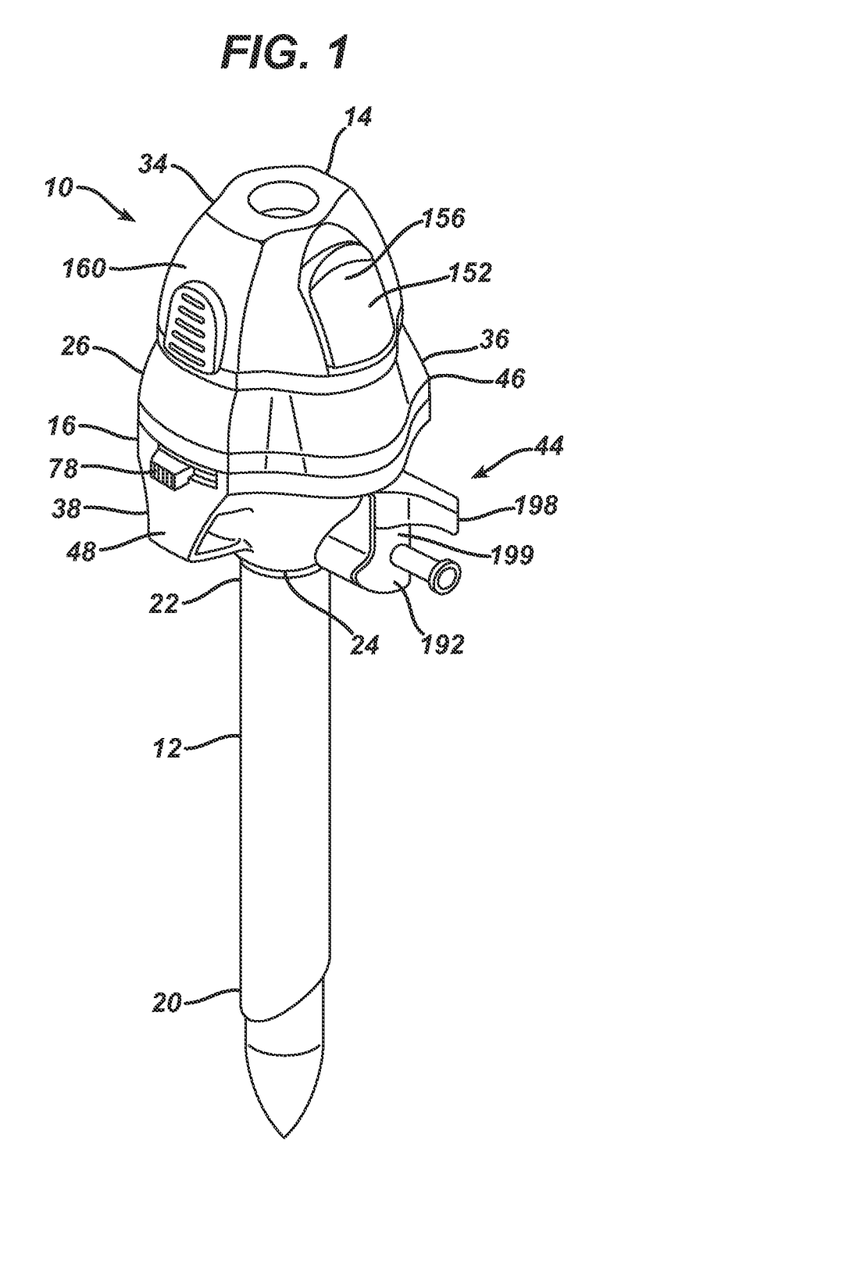
FIG. 1 is a perspective view of a trocar assembly as shown in US Patent Application publication US2005/0070947.
Figure 2:
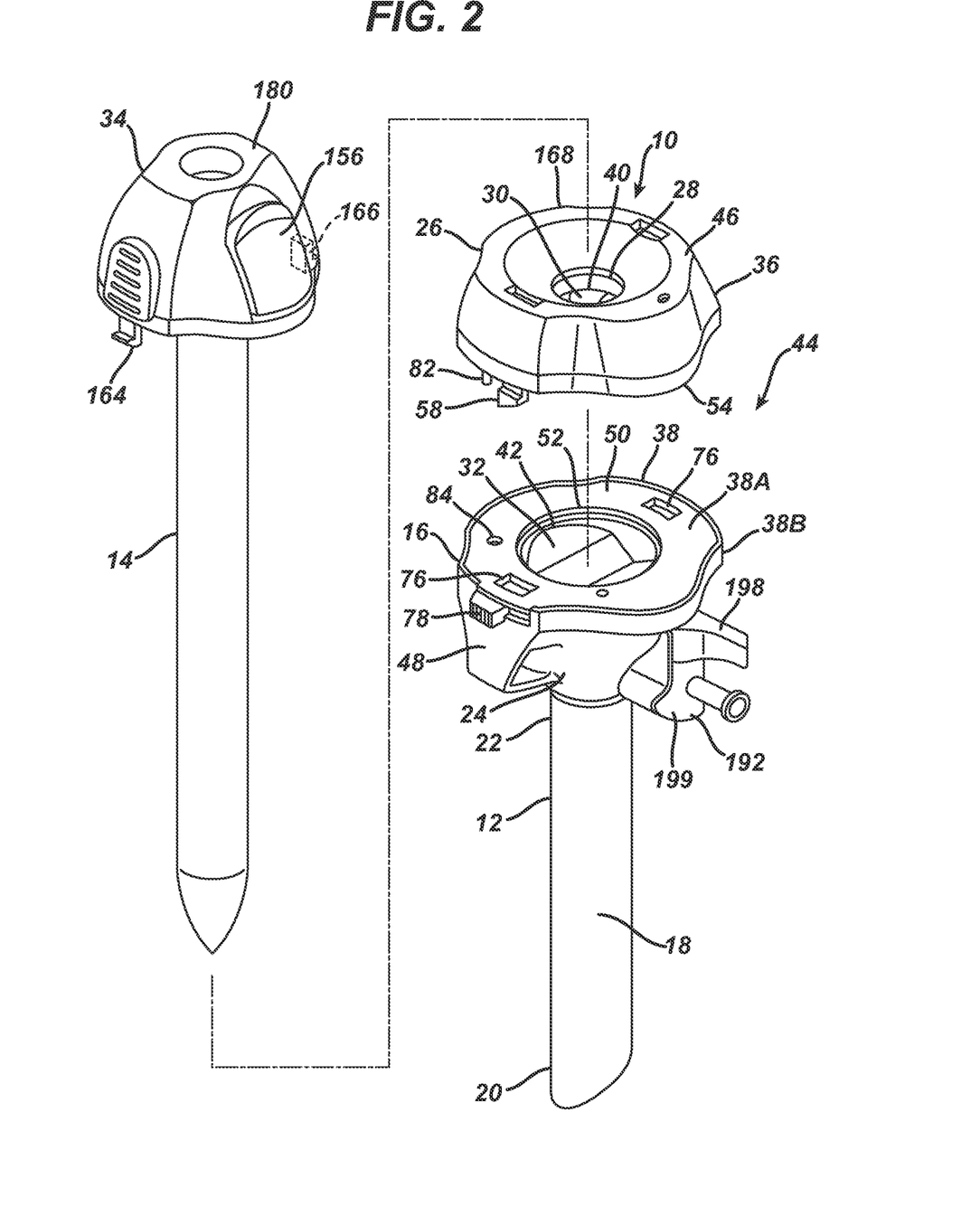
FIG. 2 is an exploded view of the trocar assembly shown in FIG. 1.
Figure 3:
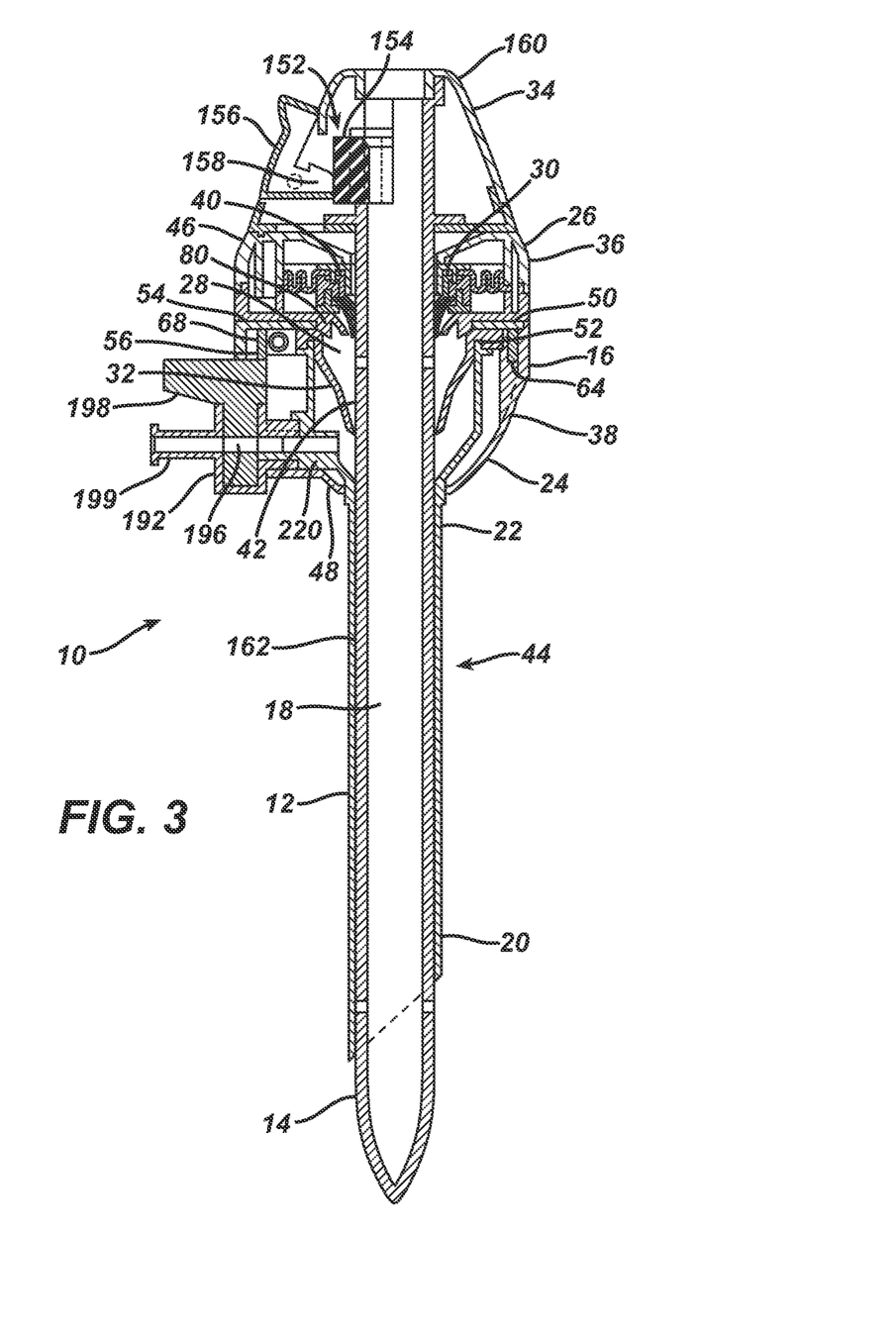
FIG. 3 is a cross sectional view of the trocar assembly shown in FIG. 1.
Figure 4:
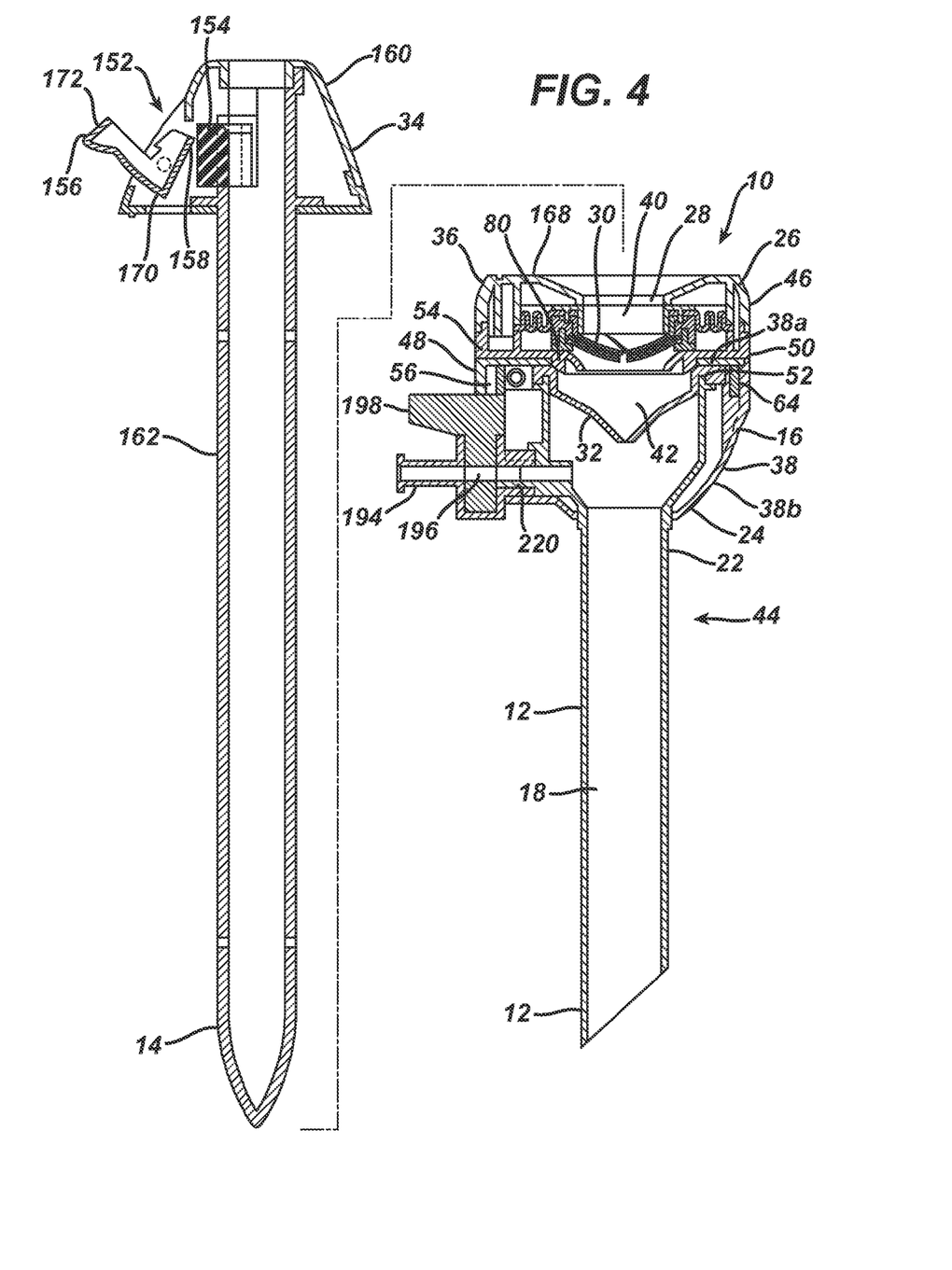
FIG. 4 is an exploded cross sectional view of the trocar assembly shown in FIG. 1.
Figure 5:
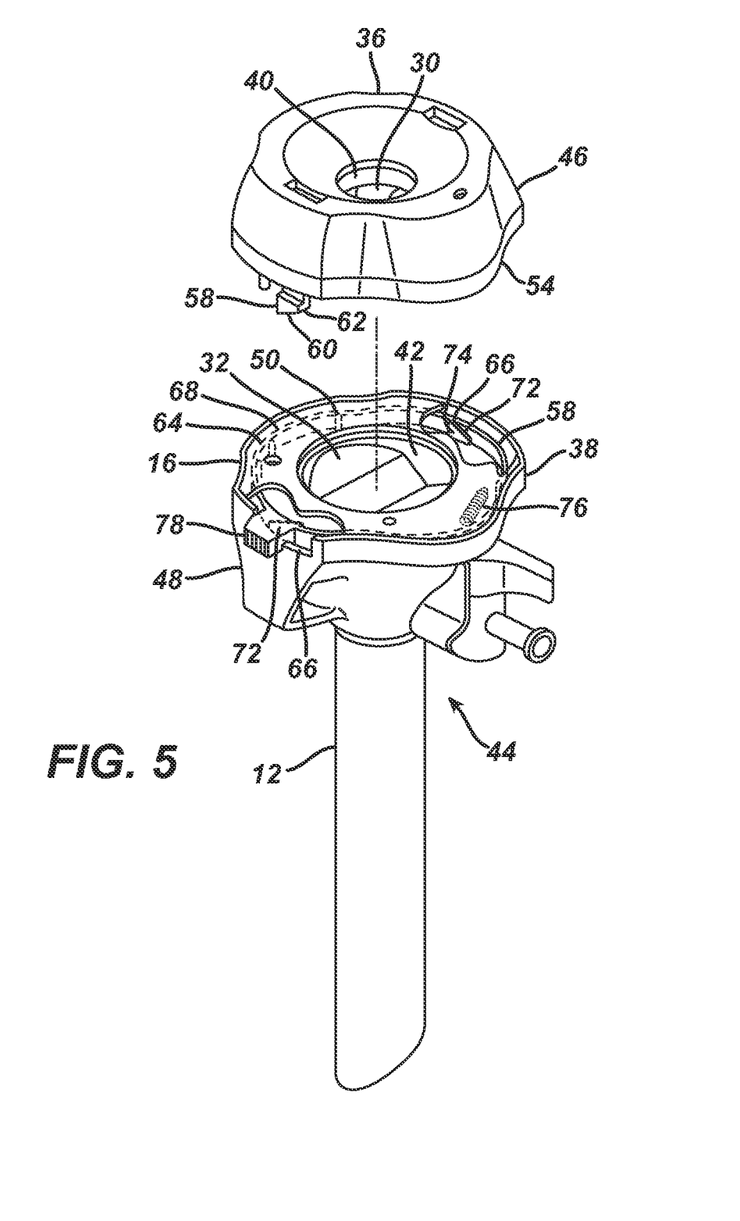
FIG. 5 is a perspective view of the trocar of FIGS. 1-4 illustrating portions of the latching assembly.

Referring to FIG. 2, the trocar housing 16 is shown with the first and second housing members 36 and 38 separated, one from the other, and with the obturator removed. The housing member 36 and housing member 38 which are selectively coupled together, so that the members 36 can be removed from the member 38. The first and second housing members 36, 38 include aligned apertures 40, 42 shaped and dimensioned for the receipt of instruments that are selectively passed through the trocar housing 16.

First and second housing members 36, 38 can be attached together during the insertion of the trocar into the abdominal wall, as well as during the normal course of a procedure. However, it can also desirable to remove the first housing member 36 during the removal of a specimen, for example, from the abdominal cavity. The removal of the first housing member 36 allows the specimen to pass through (such as by being pulled with a grasper) through the cannula 12 and the duckbill seal assembly 32, but without passing the specimen through proximal instrument seal assembly 30. This provides for easier specimen removal and less trauma to the specimen during the removal process.

The first housing member 36, which can be in the form of an upper housing cap, is shown supporting the proximal sealing assembly 30 and sits atop the second housing member 38 in which the duckbill seal assembly 32 is mounted. The first housing member 36 includes an aperture 40 extending therethrough. The proximal seal assembly 30 is positioned within the aperture 40 of the first housing member 36.

The second housing member 38 is shown supporting the duckbill seal assembly 32, with the second housing member 38 including an aperture 42 extending therethrough. The duckbill seal assembly 32 is positioned within the aperture 42 of the second housing member 38 adjacent the top surface 50 of the second housing member 38. In the trocar shown in FIGS. 1-4, the peripheral rim 52 of the duckbill seal assembly 32 is shown positioned directly adjacent the top surface 50 of the second housing member 38 for engagement with a feature (such as a rim or lip) on the lower surface 54 of the first housing member 36 to provide sealing when the members 36 and 38 are joined.

Connection of the first housing member 36 to the second housing member 38 is facilitated by a rotary latch assembly 56. In particular, the first housing member 36 includes first and second downwardly extending arms 58. Each of the downwardly extending arms 58 includes a downwardly facing camming surface 60 and an outwardly facing latching surface 62.

The second housing member 38 similarly includes a latching ring 64 (See FIG. 5) with first and second latch members 66 for respectively engaging the respective latching surfaces 62 of the first and second downwardly extending arms 58 of the first housing member 36. The latching ring 64 is axially aligned with the central axis of the trocar sleeve 44 and lies in an annular groove 68 around the perimeter of the duckbill seal assembly 32. The latching ring 64 is capable of rotating about the central axis of the trocar sleeve 44. The spring 70 holds the latching ring 64 in a locked position with a small amount of preloaded bias. However, the spring 70 allows rotation of the latching ring 64 during the attachment of the first housing member 36. The first and second latch members 66 respectively include upwardly facing camming surfaces 72 that interface with downwardly facing camming surfaces 60 of the first and second downwardly extending arms 58 of the first housing member 36.

The first and second latch members 66 each include an upwardly facing camming surface 72 shaped and dimensioned to respectively engage the camming surfaces 60 of the downwardly extending arms 58. Similarly, the first and second latch members 66 include inwardly facing latching surfaces 74 shaped and dimensioned for engaging the outwardly facing latching surfaces 62 of the first and second downwardly extending arms 58.

In practice, latching of the first and second housing members 36, 38 is achieved by passing the first and second downwardly extending arms 58 through holes 76 formed in the top surface 50 of the second housing member 38. As the first and second downwardly extending arms 58 extend through the respective holes 76 adjacent the first and second latch members 66 of the latching ring 64, the camming surfaces 60 of the respective first and second downwardly extending arms 58 engage the camming surfaces 72 of the first and second latch members 66. The engagement causes the latch ring 64 to rotate in a manner permitting the first and second downwardly extending arms 58 to extend past the first and second latch members 66. This rotation is against the bias provided by the spring 70.

Once the first and second downwardly extending arms 58 move past the first and second latch members 66, the spring 70 biasing the latching ring 64 causes the latching ring 64 to return to its original position and the outwardly facing latching surfaces 62 of the first housing member 36 engage the inwardly facing latching surfaces 74 of the second housing member 38 to securely couple the first housing member 36 to the second housing member 38. The first and second housing members 36, 38 are selectively disengaged through the actuation of a lever 78 attached to the latching ring 64. Rotation of the lever 78 causes the latching ring 64 to rotate, moving the first and second latching members 66 out of engagement with the downwardly extending arms 58.

The top surface 50 of the second housing member 38 includes holes 76 allowing the downwardly extending arms 58 of the first housing member 36 to pass through. The trocar housing 16 is disassembled by pushing the lever 78 in a horizontal rotation, causing rotation of the latching ring 64 about the central axis of the trocar sleeve 44 in a manner overcoming the spring force. The lever 78 is accessible to the surgeon through a slot in the side of the trocar housing 16. When the lever 78 is pressed/moved circumferentially, the first and second latching members 66 of the latching ring 64 rotate past the first and second downwardly extending arms 58, and the first housing member 36 is released from the second housing member 38.

The trocar shown in FIGS. 1-5 provides a seal between first housing member 36 and the second housing member 38 by using a downwardly extending flange 80 (See FIG. 3) on the lower surface 54 of the first housing member 36 to compress a perimeter portion of the duckbill seal assembly 32 adjacent the top surface 50 of the second housing member 38. The flange 80 and the duckbill seal assembly 32 include opposed angled surfaces. This provides an angular interface between the flange 80 on the first housing member 36 and the duckbill seal assembly 32 interface of the second housing member 38.

The downwardly extending flange 80 of the first housing member 36 includes an angular interface that exerts a radial force component on the duckbill seal assembly 32. The angular interface also creates a vertical force component that translates into assembly force. The radial force dilates the interfacing feature, that is, the peripheral rim 52 of the duckbill seal assembly 32. Since the vertical force is only a portion of the total normal force, the assembly force is reduced as a function of the angle of the interface.

Proper alignment between the first and second housing members 36, 38 is achieved by the provision of an alignment pin 82 extending downwardly from the lower surface 54 of the first housing member 36 and a mating hole 84 shaped and dimensioned for receiving the alignment pin 82 formed along the top surface 50 of the second housing member 38.

Trocar Having Improved Sealing

Referring now to FIGS. 6 to 16, a trocar 1000 according to one embodiment of the present invention is illustrated. The trocar 1000 may incorporate one or more of the features disclosed in US 2005/0070947, incorporated herein by reference.

Figure 6:
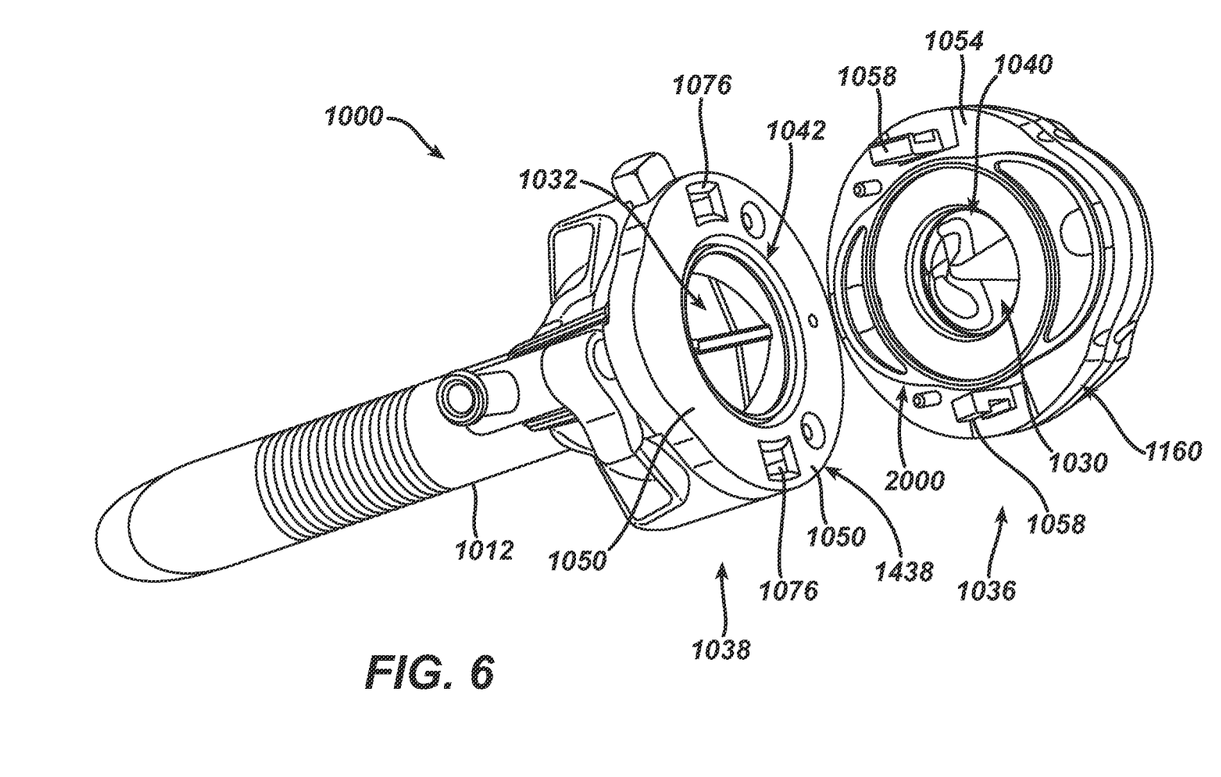
FIG. 6 is a perspective view of trocar according to one embodiment of the present invention, the trocar shown with an upper seal housing member separated from the lower seal housing member, and showing an asymmetric seal gasket overmolded to a bottom facing surface of the upper seal housing member, with the seal gasket comprising a circular portion and a non-circular portion, the seal gasket having a long (major) axis and a short axis.

As shown in FIG. 6, the trocar 1000 comprises a cannula 1012, first housing member 1036, and a second housing member 1038. In FIG. 6, the first housing member 1036 is shown separated from and rotated with respect to the second housing member 1038, so that the distal end (lower end) of the first housing member 1036 is visible, and to reveal a seal 2000 for providing sealing between upper housing member 1036 and lower housing member 1038 when members 1036 and 1038 are coupled together, such as by a latching assembly. The latching assembly may include latch arms 1058 extending from housing member 1036 and into receiving openings 1076 formed in an upper surface of housing member 1038. Seal 2000 may be formed of a material such that seal 2000 is compressed between opposed surfaces of members 1036, 1038 when members 1036, 1038 are joined together Seal 2000 is described in more detail below.

The first housing member 1036 may support a proximal seal assembly 1030 disposed in an opening 1040, and the second housing member 1038 may support a more distal (lower) duckbill seal assembly 1032 disposed in an opening 1042. Proximal seal assembly 1030 can provide sealing about (e.g. around the circumference of) an instrument (or obturator) passing through the trocar housing. Duckbill seal assembly 1032 may be employed to restrict axial flow of insufflation gas upward (along the long axis of cannula 1012) when no instrument (or obturator) is disposed in the housing.

Seal 2000 can be in the form of a gasket overmolded in a groove or recess in the lower (distally facing) surface 1054 of the upper housing member 1036. Alternatively, the seal 2000 could be overmolded in a groove or recess in the upwardly facing surface 1050 of lower housing member 1038. In still another embodiment, the seal 2000 can be separate component captured between opposed surfaces 1050 and 1054.

As explained above with respect to trocar 10 shown in FIG. 1-5, the peripheral rim 52 of the duckbill seal assembly 32 is shown positioned for engagement with a feature on the lower surface 54 of the first housing member 36 to provide sealing between the housing member 36 and 38 when the members 36 and 38 are joined.

In contrast, the seal 2000 of the present invention does not require engagement of the perimeter of the duckbill seal 1032 with a feature on the lower surface of the housing member 1036, nor registration with a rim or lip on the lower surface.

Referring to FIGS. 6-12, seal 2000 is spaced radially outward from the perimeter of the duckbill seal assembly 1032, radially outward from the perimeter of opening 1042 in the upper surface 1050 of housing member 1038, and radially outward from the perimeter of opening 1040 in lower surface 1054 of housing member 1036. Such radially outward spacing of the seal 2000 can be advantageous in resisting torsional and/or bending loads which would tend to "rock" or otherwise displace housing member 1036 with respect to housing member 1038, and which could provide for leakage of insufflations gas or other fluid from between members 1036 and 1038.

Figure 7:
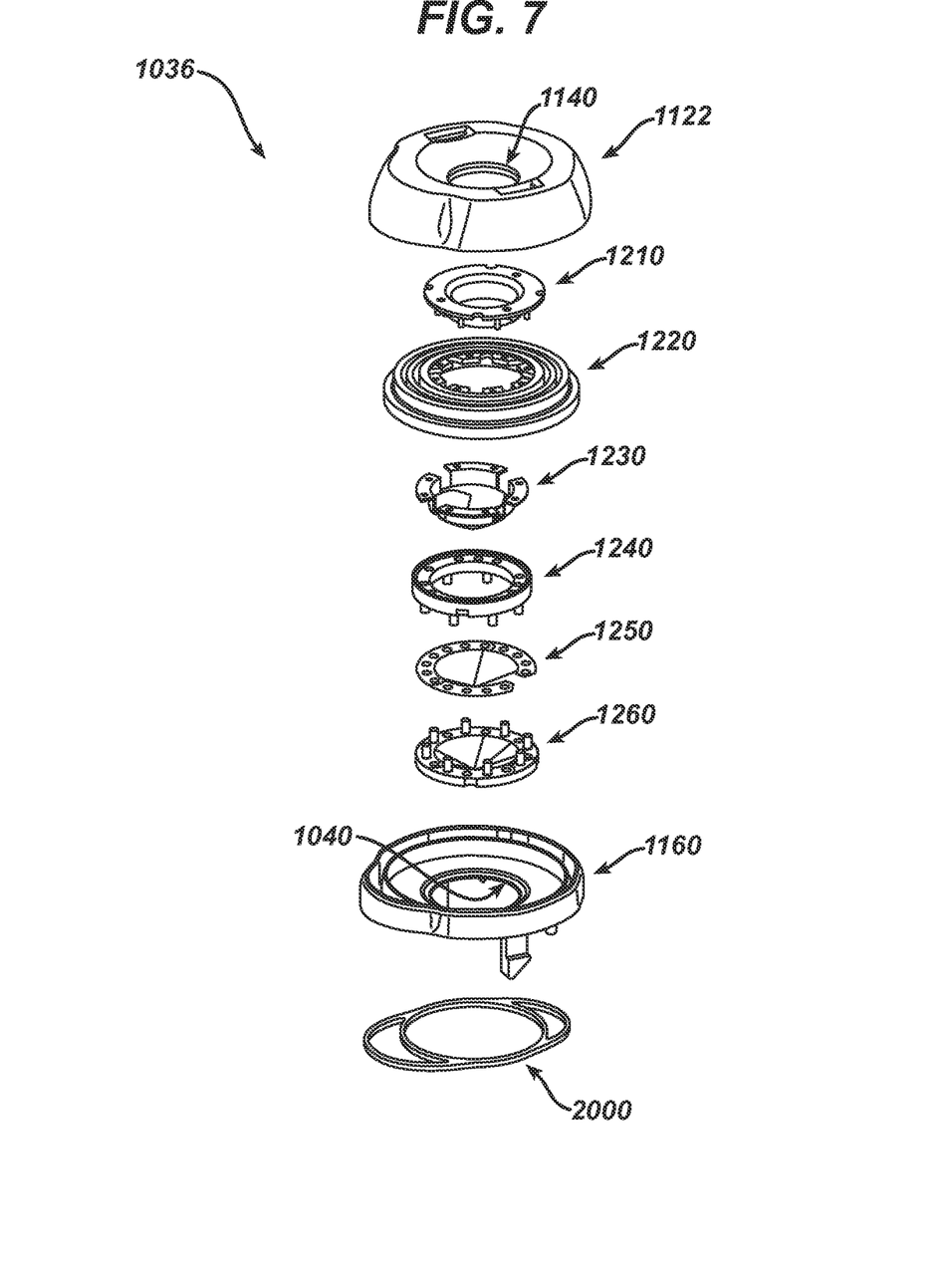
FIG. 7 is an exploded view of an upper housing member of FIG. 6.

FIG. 7 depicts an exploded view of the first (upper) housing member 1036. Housing member 1036 includes upper cap 1122 having opening 1140 therein, a lower base 1160, and seal 2000, which can be disposed on distally facing surface 1054 of seal base 1160. Cap 1122 and base 1160 can capture components of the proximal instrument seal assembly. The proximal instrument seal assembly is shown to include a crown 1210, bellows 1220, seal protector 1230, upper seal retaining ring 1240, instrument seal 1250, and lower seal retaining ring 1260.

Figure 8:
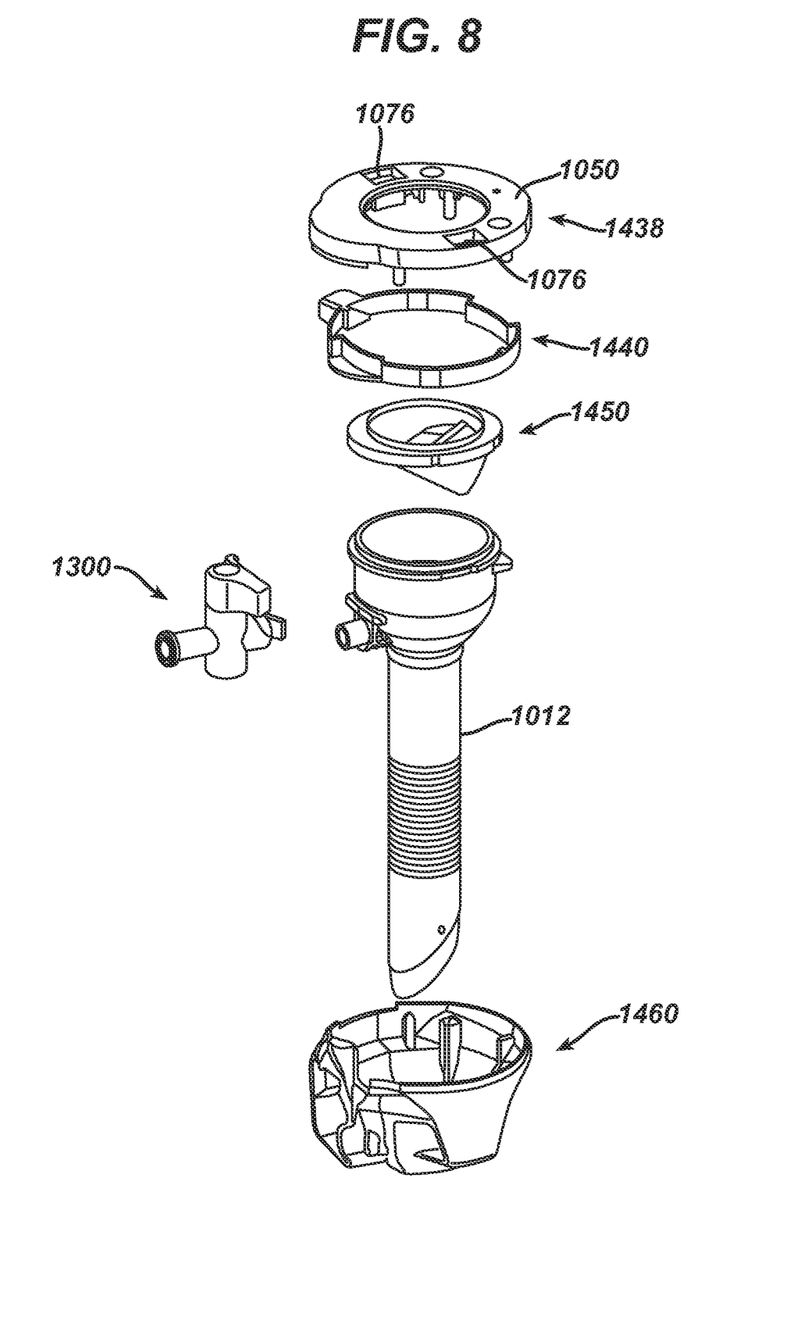
FIG. 8 is an exploded view of a cannula and components of the lower housing member shown in FIG. 6.

FIG. 8 depicts an exploded view of the cannula 1012, insufflation valve assembly 1300, and components of the second (lower) housing member 1038, including lower housing cap 1438, latch ring 1440, duckbill valve 1450, and lower housing portion 1460. As shown in FIG. 8, the housing cap 1438 may include a generally horizontal, generally planar upwardly facing surface 1050 having latch openings 1076 therein.

Figure 9:
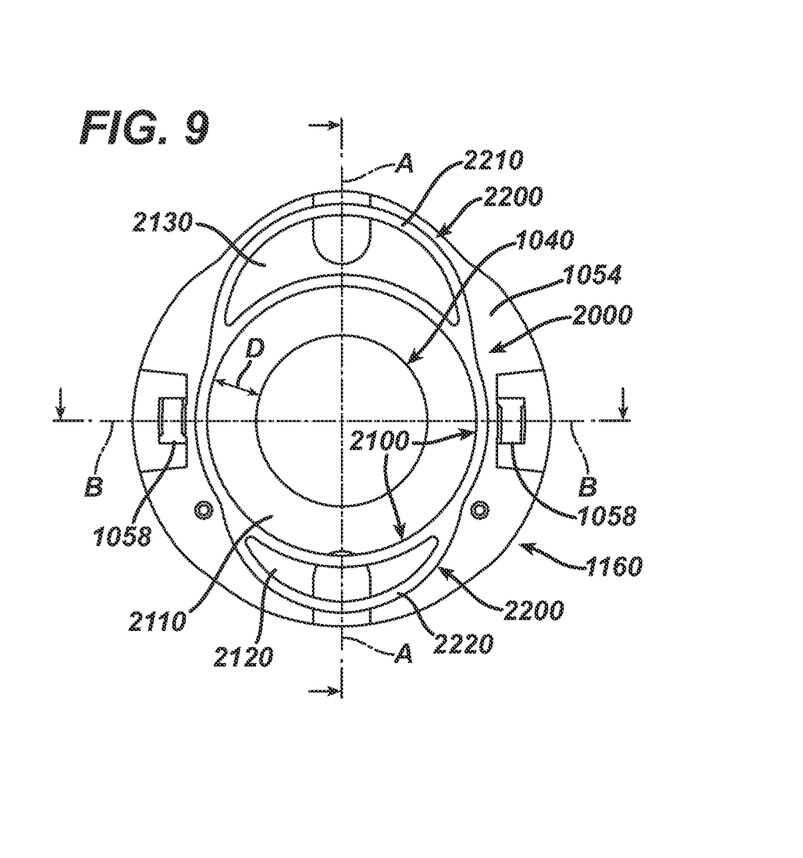
FIG. 9 is a plane view of the bottom (distal) surface of the seal base shown in FIG. 7, including a seal according to the present invention disposed in a groove in a surface of seal base.

FIG. 9 illustrates the orientation of seal 2000 with respect to various features of the seal base 1160 shown in FIG. 7. FIG. 9 is a bottom view (looking proximally from below seal base 1160). Seal 2000 can be disposed in a groove, slot, or other recess formed in the surface 1054 of seal base 1160. Seal base 1160 can be formed of a relatively harder material, such as being molded of polycarbonate or other suitable medical grade plastic or polymer. In contrast, seal 2000 can be relatively softer, and can be a separate piece, or can be overmolded to seal base 1160 in a "two shot" molding process when base 1160 is molded, such as from polycarbonate.

As can be seen in FIG. 9, the seal 2000 may have a gasket configuration, and can include a generally circular portion 2100 and a generally non-circular portion 2200. The circular portion 2100 can provide a first seal opening 2110 having a diameter greater than opening 1040 in seal base 1160. The generally non-circular portion 2200 can provide second and third seal openings 2120 and 2130. Accordingly, seal 2000 can have multiple openings to reduce the total seal surface area (as viewed in FIG. 9) and the force required to compress the seal.

The seal 2000 can be longer than it is wide, having a major axis A-A and a minor axis B-B, as shown in FIG. 9. The circular portion 2100 can be generally concentric with opening 1040, but can be offset radially outwardly from opening 1040, such as by a radial offset "D". Accordingly the diameter of the perimeter of the circular portion 2100 is shown to be larger than the diameter of opening 1040.

The non-circular portion 2200 is shown as comprising two lobe shaped gasket extensions 2210 and 2220. The lobe shaped extensions can have the same or different shapes. The lobe shaped gasket extensions are shown as each being generally symmetric about major axis A-A of seal 2000.

As shown in FIG. 9, the minor axis B-B of seal 2000 can be collinear with a diameter of opening 1040 and can extend through the latch arms 1058, so that axis B-B corresponds to a latching axis of the trocar. Major axis A-A can extend along a diameter of opening 1040 which is generally perpendicular to axis B-B. Orienting the long dimension (major axis) of the seal 2000 generally perpendicular to an imaginary axis extending though latch arms 1058 provides a larger lever arm to resist forces applied to housing 1036/1038 which may, under some loading conditions, cause "rocking" or pivoting of the upper housing member 1036 relative to lower housing member 1038 about axis B-B.

Additionally, by spacing the circular portion 2100 of seal 2000 outwardly from opening 1040 and the perimeter of the instrument seal and/or the duckbill seal, the circular portion 2100 has a larger radial distance from the center of opening 1040, and accordingly more leverage to resist leakage when the trocar is subjected to torsion or bending loads. In one non-limiting embodiment, when seal 2000 is placed in compression (such as by latching housing member 1036 to housing member 1038), the resulting compression of seal 2000 can act in the manner of a gasket preload to resist separation of housing member 1036 from housing member 1038.

Figure 10:
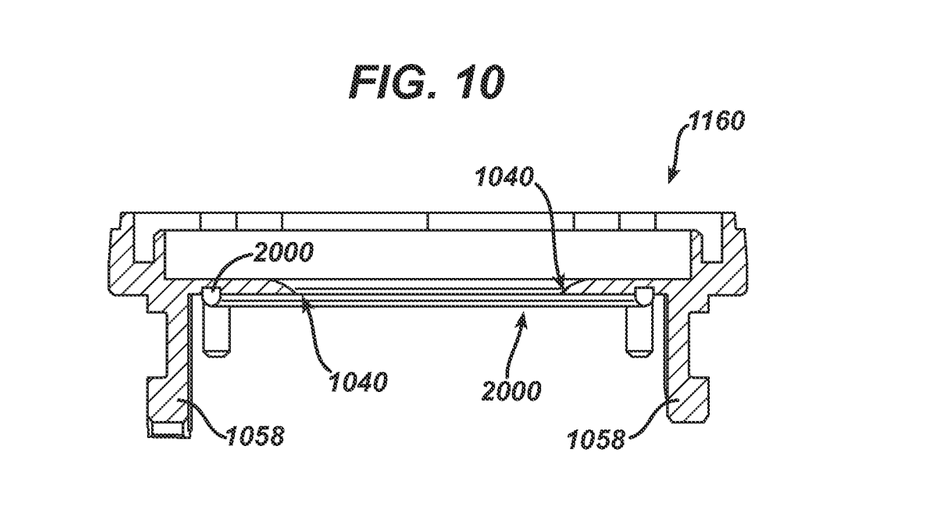
FIG. 10 is a cross sectional illustration of seal base in FIG. 7 taken along axis B-B.
Figure 11:
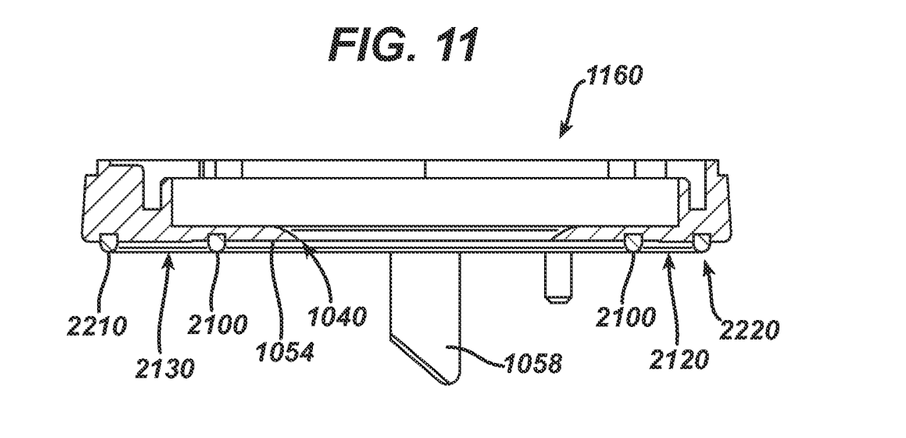
FIG. 11 is a cross sectional illustration of the seal base of FIG. 7 taken along axis A-A.

FIG. 10 is a cross-section of the seal base and seal 2000 taken along axis B-B (see arrows associated with axis B-B in FIG. 10), and FIG. 11 is a cross section taken along axis A-A. In the embodiment shown in FIGS. 10 and 11, a portion of the cross-section of the seal is disposed in a slot in the bottom surface (surface 1054) of seal base 1160, and the seal 2000 extends downwardly (distally) from the slot and bottom surface of the seal base 1160. The cross section in FIG. 10 is taken through the circular portion 2100 of seal 2000 aligned with axis B-B. In FIG. 11, the cross section is taken through both the circular portion 2100 and the non-circular portion 2200 of seal 2000.

Figure 12:
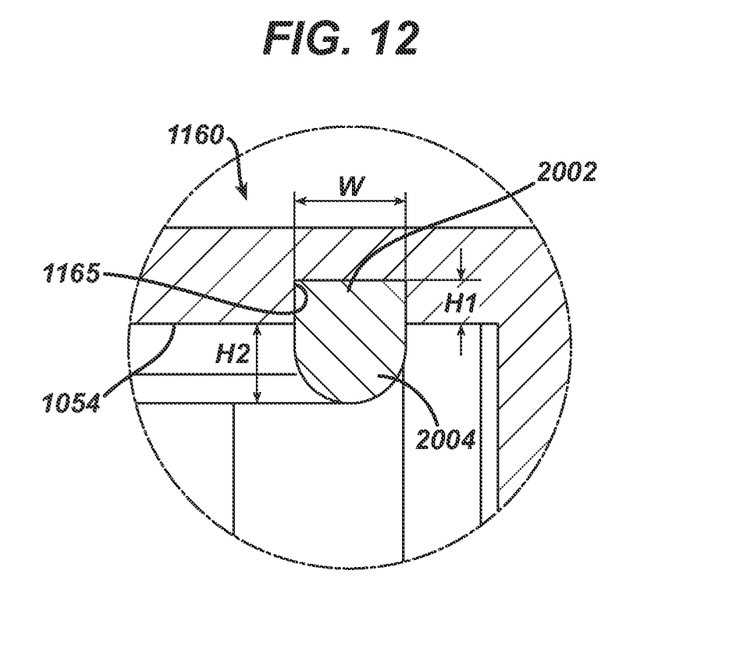
FIG. 12 is an enlarged cross sectional view of a portion of the seal in FIG. 10 shown disposed in a groove in a distally facing surface of the seal base.

FIG. 12 is an enlarged cross-sectional illustration of a the seal 2000 having a base portion 2002 disposed in a groove 1165 formed in surface 1054, and a seal contact portion 2004 extending downward from surface 1054 for providing sealing engagement with an opposing surface on lower housing member 1038 (for instance, sealing engagement with surface 1050). Seal portion 2004 can have a generally semicircular shape in cross section, so as to approximate continuous line contact around the perimeter of the seal against an opposing surface, thereby increasing the contact pressure between the seal 2000 and the surfaced against which it is compressed.

Both surface 1050 and 1054 can be formed for relatively harder materials, and seal 2000 can be formed of a relatively softer material. The seal material can have a cured/molded durometer of less than about 50 Shore A, more particularly less than or equal to about 20 Shore A, and still more particularly between about 4 and about 10 Shore A. In one embodiment, the seal 2000 can have a Durometer, Type 00 of about 40. The seal 2000 can be formed of a relatively soft material and dimensioned to avoid requiring a large compressive force/clamping force when seal 2000 is compress upon latching housing members 1036 and 1038 together. In particular, the combined area of the openings 2110, 2120, and 2130 enclosed by the seal 2000 can be larger than the combined area (as viewed in FIG. 9) of the circular and non circular portions of the seal 2000 that are compressed when housing members 1036 and 1038 are joined.

In one non-limiting embodiment, the seal 2000 can be comprise a silicone rubber over molded to be supported in a slot in surface 1054. A suitable liquid silicone rubber is commercially available as MED-4901 from NuSil Technology of Carpinteria, Calif. Another suitable seal material is COHRLASTIC R-10470 Medium General Purpose Silicone Sponge available from Stockwell Elastomerics, an authorized supplier of Saint-Gobain products. Other seal materials include Poron 4790-92 Urethane gasket material and Bisco BF-1000 Silicone gasket material. A lubricant, such as NuSil Med 361 or 400 can be applied to the seal 2000 to assist in sealing.

The seal cross section shown in FIG. 12 is in depicted in an uncompressed state, prior to joining (such as by latching) housing member 1036 to housing member 1038. While various seal materials and seal dimensions may be employed, in one embodiment the groove 1165 can have a generally uniform groove depth H1 between about 0.010 and about 0.025 inch, and more particularly between about 0.015 inch and about 0.020 inch. The seal 2000 can have a free, uncompressed height H2 above the groove and surface 1054 of between about 0.010 inch and about 0.060 inch, more particularly between about 0.025 inch and about 0.045 inch. The seal 2000 can have a cross-sectional width W of between about 0.050 inch and about 0.074 inch.

Figure 13:
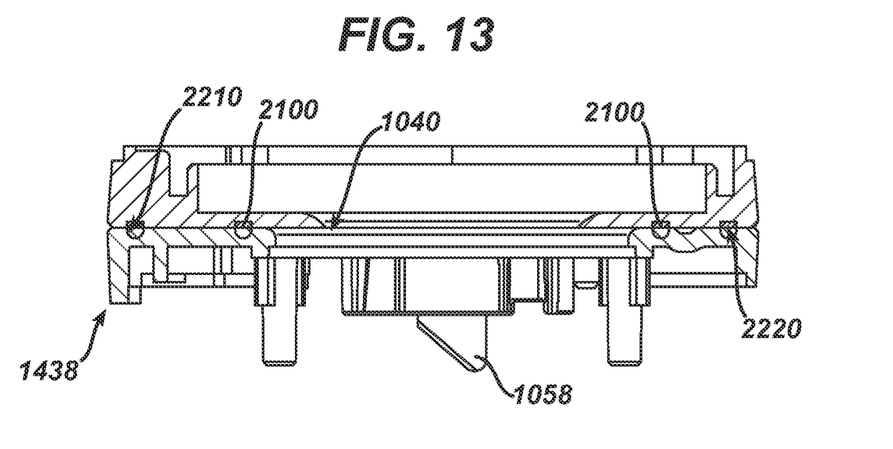
FIG. 13 is a partial cross-sectional illustration showing the seal base and lower housing cap joined together (such as by the latching assembly), so as to compress the gasket seal between opposing surfaces.

FIG. 13 is a partial cross-sectional illustration showing the seal base 1160 and lower housing cap 1438 joined together (such as by the latching assembly), so as to compress seal 2000 between opposing surfaces of base 1160 and cap 1438. FIG. 13 is a cross-sectional illustration taken along an axis corresponding to axis A-A in FIG. 9, such that the seal 2000 is visible as four cross-sections in the section view.

Figure 16:
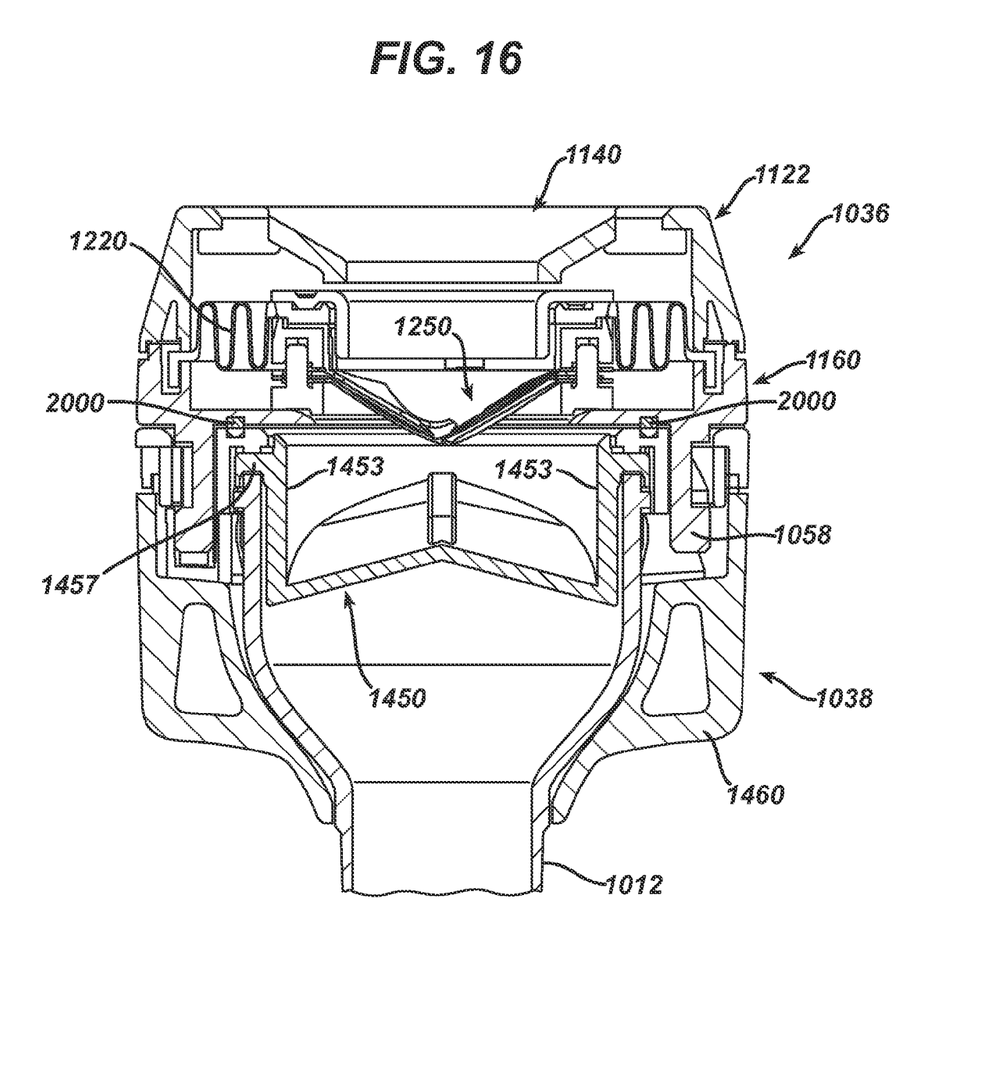
FIG. 16 is a partial cross-sectional illustration taken along an axis corresponding to axis B-B in FIG. 9, and showing in cross section the upper and lower housing members joined together.

FIG. 16 is a partial cross-sectional illustration taken along an axis corresponding to axis B-B in FIG. 9, and showing in cross section the upper and lower housing members joined together. FIG. 16 illustrates the position of instrument seal 1250 and the duckbill seal 1450 having inner wall 1453. As seen in FIG. 16, the seal 2000 is radially offset outward of the inner wall 1453 of the duckbill seal 1450.

Figure 14:
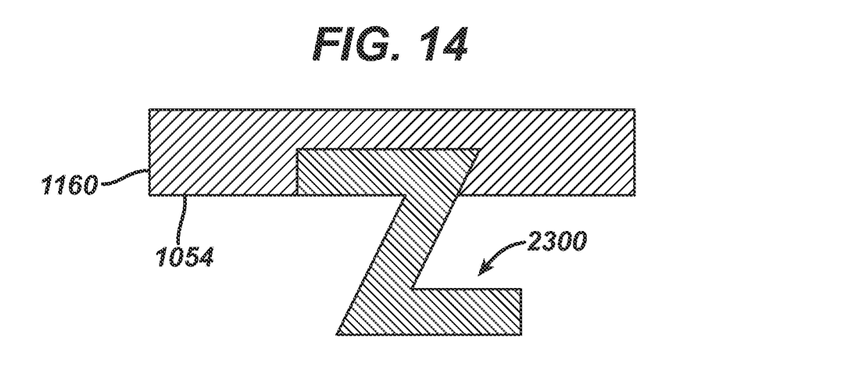
FIG. 14 illustrates an alternative seal cross section having a generally Z shaped configuration.
Figure 15:
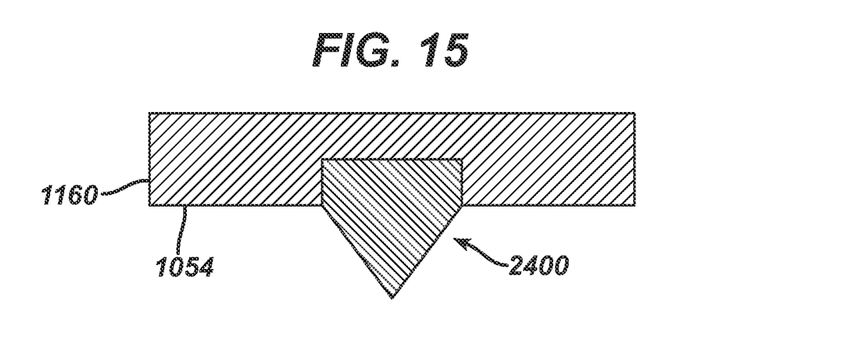
FIG. 15 illustrates an alternative seal cross section having a generally V-shaped configuration.

FIGS. 14 and 15 illustrate alternative seal cross-sectional configurations. FIG. 14 illustrates a seal cross section 2300 having a generally Z shaped configuration. FIG. 15 illustrates a seal cross section 2400 having a generally V-shaped configuration with a relatively pointed tip for engaging an opposing surface.

While one or more embodiments have been shown and described, it will be understood that there is no intent to limit the invention by such disclosure, but rather, is intended to cover all modifications and alternate constructions falling within the spirit and scope of the invention as defined in the appended claims.

What is claimed:

1. A surgical access device comprising:
   a first housing member;
   a second housing member;
   wherein the first and second housing members are configured to be releasably coupled one to the other;
   wherein the first and second housing members include generally aligned apertures shaped and dimensioned for passage of an instrument therethrough; and
   a seal offset radially outwardly from the aligned apertures, the seal configured to restrict fluid flow intermediate the first and second housing members, the seal comprising an inner portion defining a first seal opening and an outer portion co-planar with and connected to an inner circular portion to define two crescent shaped seal openings laterally offset from the first seal opening.

2. The access device of claim 1 wherein one of the first and second housing components support an instrument seal, and wherein the other of the first and second housing components supports a zero closure seal.

3. The access device of claim 1 wherein the seal has a durometer of less than about 10 Shore A.

4. The access device of claim 1 wherein the seal has a durometer of between about 4 and about 6 Shore A.

5. The access device of claim 1 wherein the seal extends between about 0.025inch and about 0.045 inch from a surface associated with one of the first and second housing components.

6. The surgical access device of claim 1, wherein the inner portion is circular.

7. The surgical access device of claim 1, wherein the outer portion is non-circular.

8. A trocar comprising:
   a cannula having a passageway extending in an axial direction;
   a housing disposed at a proximal end of the cannula, the housing having a proximal opening for receiving an instrument, and the housing comprising first and second housing components configured to be selectively coupled together;

a first seal operative to seal around the instrument passing through the housing;

a second seal operative to restrict fluid flow in an axial direction when no instrument extends through the housing; and a deformable seal separate from the first and second seals, the deformable seal operative to restrict fluid flow between generally opposed portions of the first and second housing components when the first and second components are coupled together, the deformable seal comprising an inner circular portion defining a first seal opening and an outer non-circular portion co-planar with and connected to an inner circular portion to define two crescent shaped seal openings.

* * * * *